United States Patent [19]

Peltier

[11] Patent Number: 5,382,410

[45] Date of Patent: * Jan. 17, 1995

[54] ELECTROSTATIC VAPOR/AEROSOL GENERATOR WITH METHOD AND APPARATUS FOR CONDITIONING BUILDING SPACES

[75] Inventor: Mark E. Peltier, Minneapolis, Minn.

[73] Assignee: In-Vironmental Integrity, Inc., Minneapolis, Minn.

[*] Notice: The portion of the term of this patent subsequent to Mar. 23, 2010 has been disclaimed.

[21] Appl. No.: 34,297

[22] Filed: Mar. 22, 1993

Related U.S. Application Data

[63] Continuation-in-part of Ser. No. 667,200, Mar. 11, 1991, Pat. No. 5,196,171.

[51] Int. Cl.6 ............................................. A62B 11/00
[52] U.S. Cl. ........................................ 422/121; 422/5; 422/22; 422/124; 422/305; 239/34; 239/44
[58] Field of Search ................. 422/4, 5, 22, 121–125, 422/305; 237/34, 44; 261/75, 99, 100

[56] References Cited

U.S. PATENT DOCUMENTS

| | | |
|---|---|---|
| 2,140,516 | 12/1938 | Cowan . |
| 2,692,327 | 10/1954 | Avrigan . |
| 2,931,880 | 4/1960 | Yaffe . |
| 3,431,393 | 3/1969 | Katsuda . |
| 3,518,409 | 6/1970 | Corbett . |
| 3,610,879 | 10/1971 | Katzman et al. . |
| 3,633,881 | 1/1972 | Yurdin ............................ 239/44 |
| 3,659,078 | 4/1972 | Rudstrom . |
| 3,714,392 | 1/1973 | Katzman et al. . |
| 3,771,233 | 11/1973 | French et al. ............... 422/121 |
| 4,400,332 | 8/1983 | Pollard et al. . |
| 4,419,302 | 12/1983 | Nishino et al. . |
| 4,776,515 | 10/1988 | Michalchik . |
| 4,829,996 | 5/1989 | Noakes et al. . |
| 4,928,881 | 5/1990 | Barlics et al. ............... 239/44 |
| 5,196,171 | 3/1993 | Peltier ............... 422/121 |

Primary Examiner—Timothy M. McMahon
Attorney, Agent, or Firm—Moore & Hansen

[57] ABSTRACT

The controlled generation of vapors and/or aerosols from liquids is accomplished by applying a regulated, DC voltage to a wicklike, porous emitter or generator assembly which is supplied with the desired liquid to be vaporized. An electrostatic charge is applied to the liquid by means of an electrode positioned in contact with the wick assembly and connected to the DC power supply. The wick assembly includes a porous, capillary material, such as braided fibers, through which the liquid passes to exposed, vapor-emitting fiber tips.

The environment in a room, enclosed spaced of any kind, or a building may be aromatically conditioned and/or have its quality modified and enhanced by using a selected liquid conditioning substance such as an aromatic oil, deodorant, disinfectant, fumigant, fungicide, insecticide, or bactericide. Charged, conditioning vapors may be discharged into the circulating air of a building air conditioning system by mounting an emitter assembly within an air handling duct, directly in the moving air stream.

19 Claims, 7 Drawing Sheets

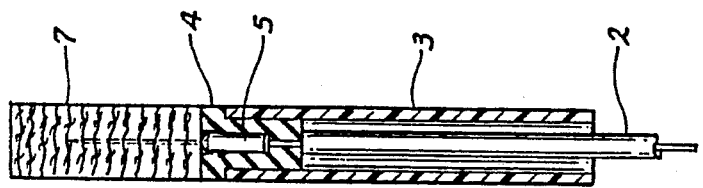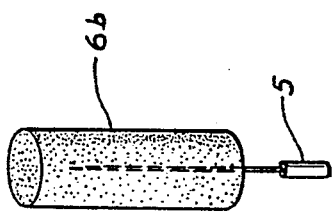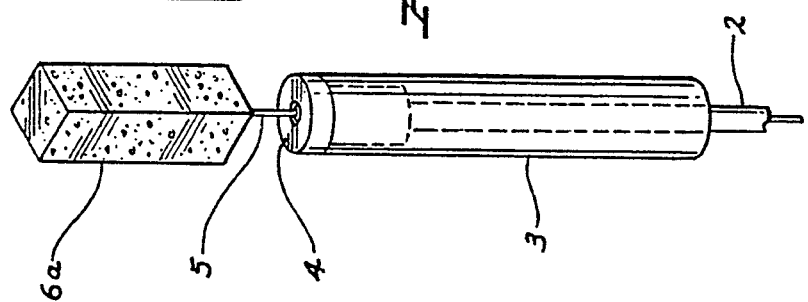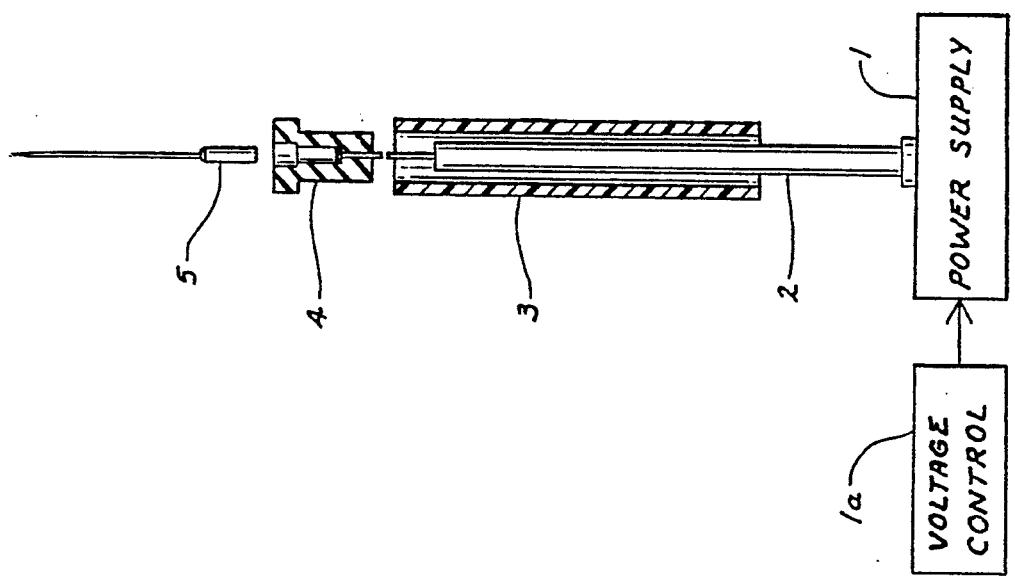

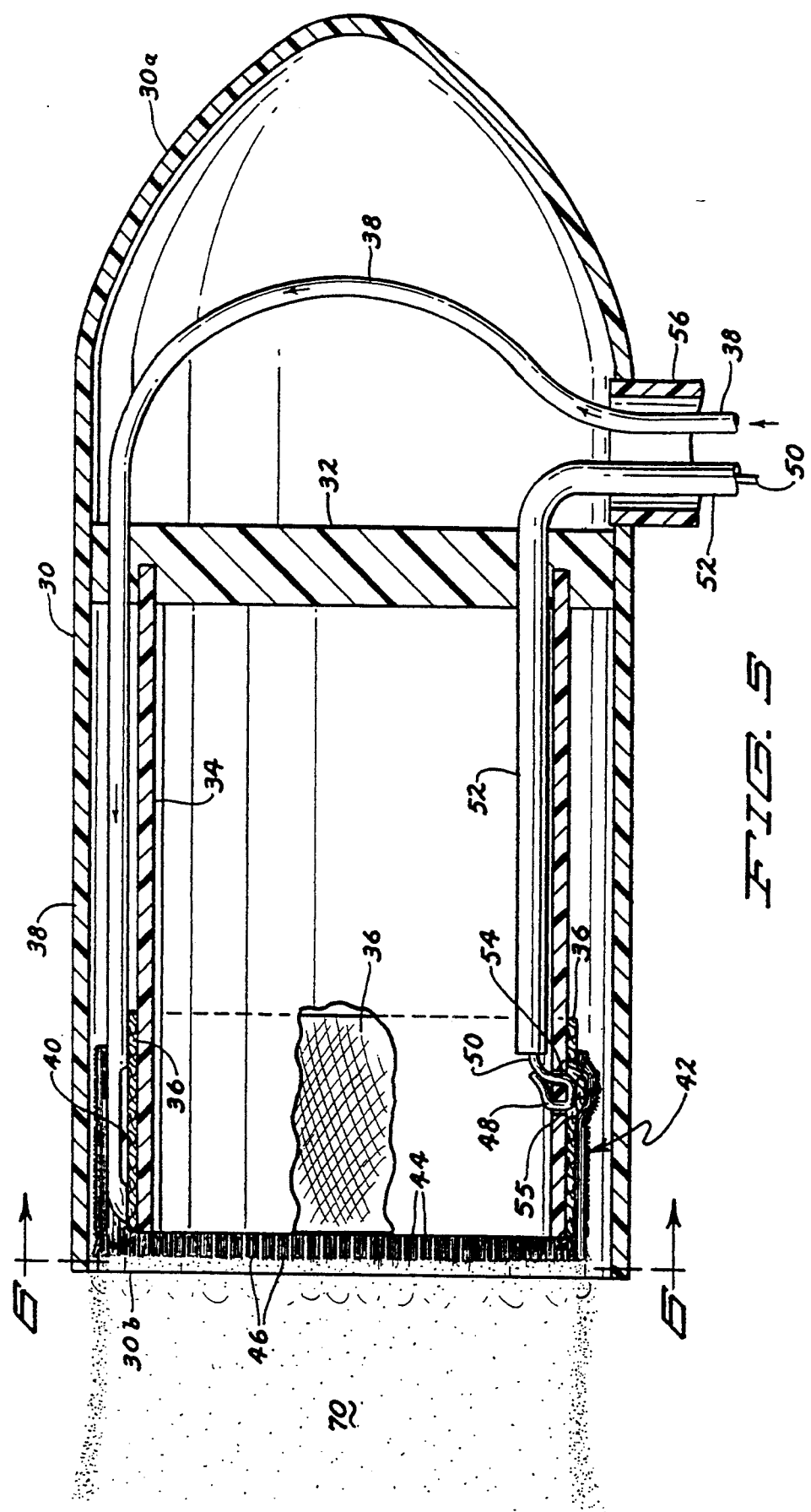

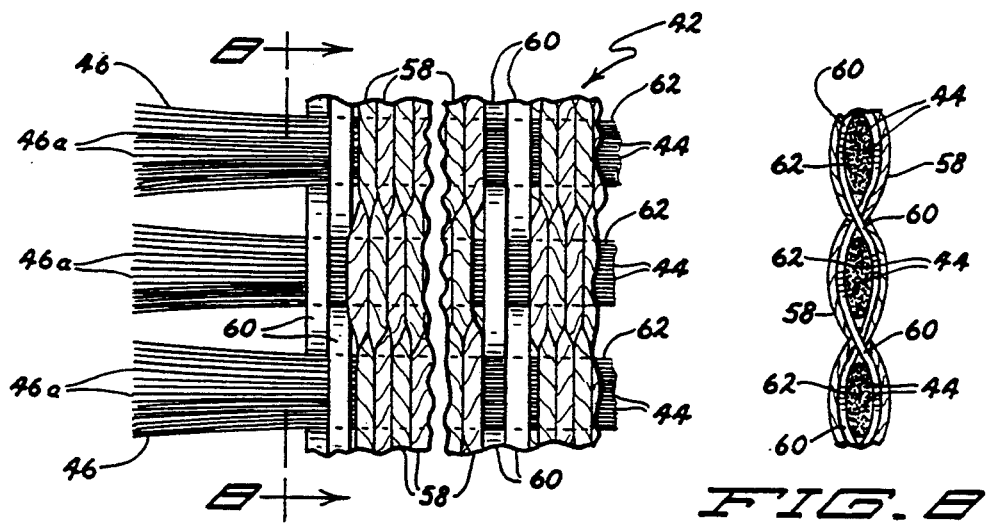
FIG. 7
FIG. 8
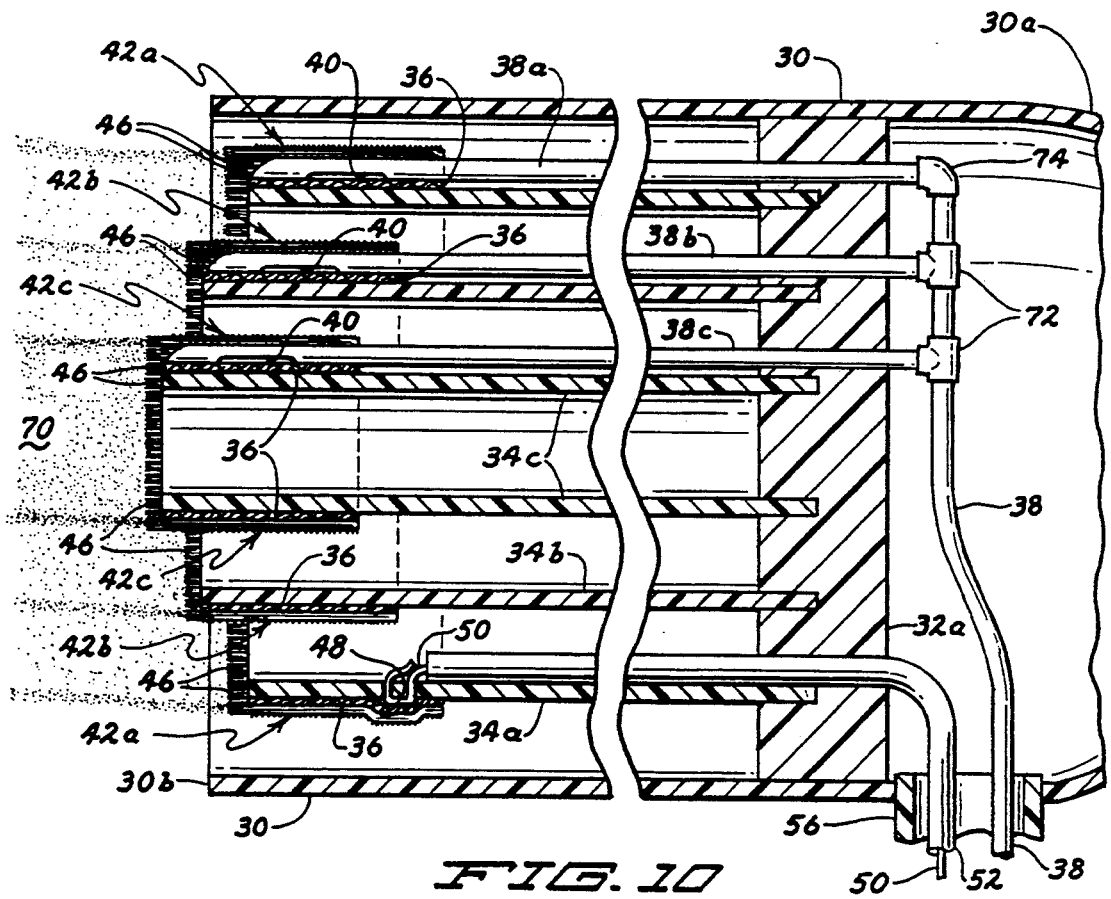
FIG. 10

ELECTROSTATIC VAPOR/AEROSOL GENERATOR WITH METHOD AND APPARATUS FOR CONDITIONING BUILDING SPACES

This application is a continuation-in-part of application Ser. No. 07/667,200 filed Mar. 11, 1991, entitled Electrostatic Vapor-Aerosol Generator and issuing Mar. 23, 1993 as U.S. Pat. No. 5,196,171.

BACKGROUND OF THE INVENTION

1. Field of the Invention

This invention in general comprises an apparatus and method for generating electrostatically charged vapor and/or aerosols from a selected family of liquids. It is intended to be used to treat or condition the air of an occupied space or building by introducing vapors which have a pleasant aroma and may also have a biocidal or biostatic effect within a building's ventilation system duct work and air handling components. It is believed that the electrostatically charged vapors and aerosols will have a greater effect upon the treatment of the air within buildings. The apparatus and methods used herein may be used to treat or condition air either by direct discharge into an enclosed space or by release of charged, conditioning vapors into air handling ducts.

There is a growing concern in the area of indoor air quality often referred to as "sick building syndrome." The modern living and working environment has been designed around energy efficiency and not so oriented around occupant health and comfort. It would be desirable to be able to recreate the properties of fresh outdoor air, indoors. Over the last five years there has also been an increased interest in aromatic essences from plants and their application to enhancing or altering the quality of indoor environment.

The primary function of the apparatus is based upon the principles outlined in the above-identified, copending U.S. patent application.

By applying a high voltage DC charge to a semiconductive, capillament assembly which receives the selected liquid, electrostatically charged vapor and aerosols will be released. This device is referred to throughout this disclosure as a "vaporizing emitter." This invention has a particular application in the vaporization of essential oils commonly used in the fragrance industry. Essential oils derived from plants, trees and flowers, also perfumes, natural and synthetic; deodorants, disinfectants, fumigants, fungicides, insecticides, and other liquid substances which are primarily hydrocarbon based which may be intended to modify, condition, or alter the quality of an indoor or outdoor atmosphere can be vaporized more effectively using this apparatus.

The vaporization of liquids is known to be accomplished by a variety of devices and there are also many devices which use electrostatic means to generate aerosols. This invention is directed to the generation of vapor and/or aerosols more efficiently from a variety of liquids with more control than the prior art.

2. Prior Art

The closest prior art was found to be an apparatus for generating a mist of negatively charged liquid aerosols, as disclosed by Michalchik in U.S. Pat. No. 4,776,515. The limitations of the patent are that a very specific conductivity of the liquid is required and that charged particles are generated, not a vapor. The device also has specific requirements upon the manner in which the liquid is fed to the capillary in order to maintain the desired aerosol generating effect.

An apparatus for producing a spray of liquid droplets of a specific size range is disclosed in U.S. Pat. No. 4,829,996. This device is specific to the production of particles by electrostatic means of a certain size and specifically not a vapor. This device is specifically an electrostatic spray generator for an inhaler.

The electrostatic dispersal of liquids by Pollard et al in U.S. Pat. No. 4,400,332 is specific in the use of a porous material having a series of termini which is fed a liquid, namely petrol fuels. This porous material is charged electrostatically and a spray of fine particles is formed in an air stream. This device produces very fine particles within an air stream wherein an annular enclosure is required. Here again vapor is not mentioned and a moving air stream is required.

Electrostatic enhancement of evaporation by French et al in U.S. Pat. No. 3,771,233 involves a method of specifically improving the evaporation of water from investment cast ceramic molds using an electrostatic charge placed upon the mold. The evaporation process is enhanced with a series of needles of an opposite charge placed near the surface of the mold. This method is specific to the evaporation of water from investment castings. In this case, evaporating water is the only objective.

This invention is an improvement upon these methods and others such that both vapor and/or aerosols can be generated from the same device. Another advantage is that the rate of vapor generation can be controlled by the adjustment of the voltage applied to the "emitter," and/or by the liquid feed rate and/or the placement of an electrostatic field forming control grid near the emitter.

BRIEF SUMMARY OF THE INVENTION

The principal object of the present invention is to generate electrostatically charged vapors and aerosols from a liquid using high voltage DC which is applied to a vaporizing emitter assembly.

An additional object of this invention is to be able to precisely control the quantity of vapor, and/or aerosols generated by controlling the voltage applied and thereby the electrostatic charge and the quantity of liquid fed to the emitter or wick.

Additional objects of this invention are to release these charged vapors and aerosols directly into the air of a room, or onto the inner surfaces of ventilation system duct work of a building or onto the surfaces of ventilation system mechanical equipment and/or to distribute the vapor/aerosols throughout a building through the ventilation system.

A further object is to be able to control the release of electrostatically charged vapors and aerosols into the atmosphere of an industrial manufacturing process or toxic environment containing substances which would be neutralized, modified, or otherwise effected by the charged vapors.

The final object of this invention is to select specific liquid chemical formulations which in vapor phase and/or aerosol form may be electrostatically charged, will have properties such that when they are introduced into the air of a room or a building ventilation system, they will modify the character and quality of the air by adding natural aromas, synthetic scents or combinations which may also include disinfection agents, fungicides, bactericides, viruscides and related formulations which could be used to disinfect building ventilation duck work and related ventilation system equipment.

In a first embodiment, a high voltage DC power supply with an adjustable output (5-50 kilovolts negative) is used to power an "electrostatic wick" assembly which is comprised of a central conductive electrode, an outer porous capillary material, and a vial, vessel, or tubular enclosure used to contain and direct the liquid to be vaporized. If the liquid is supplied to the apparatus by the use of a tube or pipe and if there is no requirement to "wick" the liquid, then the device is referred to as a "vaporizing emitter." In both devices the main components of the wick or emitter would be summarized as an electrostatically charged, liquid-fed, semi-conductive, porous, capillary assembly.

These "wicks" and "emitters" were fabricated from the following materials in hundreds of combinations in order to obtain the best vapor/aerosol generation performance for the test liquid and also the optimum air ionization output: conductive foam, ceramic fibers, graphite fibers, porous ceramic, porous polyethylene foam, porous sintered metals (discs, tubes, spheres, and sheets of stainless steel and brass), glass wool, Fiberglass braiding, graphite braiding, stainless steel braiding, class tubing, polycarbonate tubing, wood wicking, wool felts, and other materials used alone and in combination.

In a further embodiment, a high voltage, DC power supply with a fixed or adjustable output (5-50 kilovolts negative) is used to power a "vaporizing emitter" assembly which is comprised of a nonconductive tubular support over which is placed at one end an emitter sleeve comprised of a combination of fibers interwoven in a ribbonlike configuration to form bundles of distinct capillaments longitudinally oriented and freely extending at their terminal ends beyond the end of the support tubing. The freely extending terminal ends of the capillament bundles serve as charged vapor discharge sites. Preferably, the terminal ends of the capillament bundles assume brushlike configurations of distinct bundles of fibers which, if viewed at their ends, comprise dozens or hundreds of small bristle groups.

The aforesaid fibrous assembly is comprised primarily of nonconductive materials. Distinct conductive fibers or wires may be optionally interwoven with the nonconductive fibers to serve as an aid to the transfer of an electrostatic charge to the ends of the capillament bundles. An electrode is placed in conductive relation to the aforesaid emitter sleeve, either directly, or by way of contact with an inner sleeve which may facilitate wicking of liquid to the emitter sleeve. The selected liquid is supplied to the aforesaid assembly from tubing by way of a fluid control system incorporating a supply pump.

These charged "wicks" or "emitters" directly effect the natural vapor pressure of any liquid which is applied to them at any given temperature and atmospheric pressure by using electrostatic forces acting upon the surface tension of the liquid held within a porous mass, wicking, or emitter assembly.

Advantageously, the aforesaid vaporizing emitter assembly may be supported within an air duct of the central, air handling system for a building so as to discharge conditioning, charged vapors directly into the circulating air stream. In a preferred embodiment this is done by a support conduit extending through the wall of a duct, with the conduit also beneficially serving to carry the high voltage conductor lead and a liquid supply tube directed to the emitter assembly.

These and other objects and advantages of the invention will become readily apparent as the following description is read in conjunction with the accompanying drawings wherein like reference numerals have been utilized to designate like elements throughout the several views.

BRIEF DESCRIPTION OF THE DRAWINGS

FIG. 1a shows the most basic embodiment of the concept of the use of electrostatic charges to vaporize a liquid directly from a porous mass or wick. Also shown are the basic components in exploded view.

FIGS. 1b-1d show different wick embodiments;

FIG. 5 is a section view in side elevation of an electrostatic vaporization assembly utilizing a modified form of wick assembly;

FIG. 7 is a fragmentary view, on an enlarged scale of an end segment of the ribbontype vaporizing emitter element of FIGS. 5 and 6;

FIG. 8 is a section view of the emitter element of FIG. 7 taken along lines 8—8 thereof;

FIG. 10 is a section view in side elevation of a modified embodiment of vaporization assembly utilizing multiple, concentric emitters.

DETAILED DESCRIPTION OF THE PREFERRED EMBODIMENTS

Figure 2:
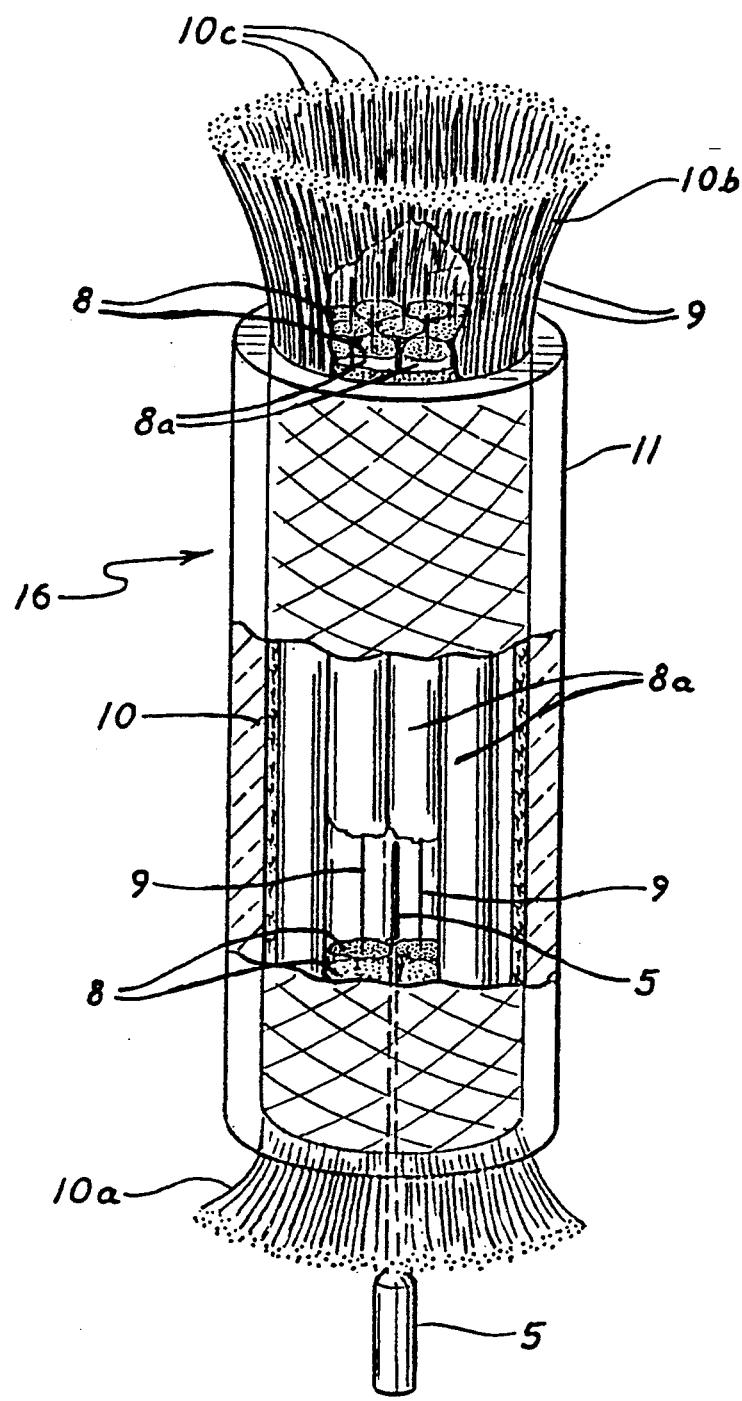
FIG. 2 is a perspective view of a preferred embodiment of a "wick" assembly partially in section.

In consideration of the drawing submitted and the partial list of materials used to construct these vaporizing emitters, it is not possible to illustrate every combination. These serve as examples that have proven to be effective under test and have demonstrated the concept of the electrostatic vaporization of selected liquids.

FIGS. 1a-1c illustrate the most basic embodiments of the "electrostatic wick" assembly and its power source. FIG. 1a shows an exploded view of the components. A high voltage DC power supply 1 with an adjustable output 1a (5-50 kilovolts negative 2-200 microamps) supplies power to a terminal 4 via a high voltage wire conduit 2. An electrode 5 is inserted in the terminal and provides the charge to the wick assemblies. High voltage terminal 4 is inserted into a plastic, e.g., polycarbonate, tube 3 as a support.

FIG. 1b is a view of these components fully assembled. The electrode is inserted into the wick material or assembly 6a, the desired liquid is supplied to the wick and power is applied at the desired voltage. The properties of the materials that comprise the wick have a significant effect upon the vapor and/or aerosol output efficiency at any given voltage setting. The porosity, conductance, and shape of the materials will determine the vapor-aerosol radio.

In FIG. 1*b* the wick material 6*a* is a conductive, carbon-treated foam, which is saturated with the desired liquid and charged by the power supply 1. In this embodiment of the wick, the foam emanates a very strong vapor from all exposed surfaces with the greatest concentration coming from the corners and edges. Wick 6*b* as shown in FIG. 1*d* is comprised of porous sintered metal. A variety of shapes and metal types were saturated with liquid and placed onto the electrode. As with the carbon foam, they also generated vapor with the greatest concentration coming from the corners and edges. This follows the general rule that corona discharge will form at points or sharp radius edges. The liquid that is near these areas is carried away by this discharge forming an electrified vapor.

FIG. 1*c* shows an embodiment of the same electrode support as in FIG. 1*b* with a wick 7 that is fabricated from a nonconductive porous material such as wool felt, porous polypropylene or similar material. The wick material is saturated with the desired aromatic liquid. The electrode is preferably inserted into the wick so that the entire electrode is covered by the wick. In this embodiment, the wick must conduct the full charge that is supplied to the electrode. The liquid provides a means of conducting the charge from the center of the wick to the outer surfaces where vaporization take place in the same manner as the wicks that are conductive. This embodiment requires a higher voltage to generate the same amount of vapors as the wicks described in FIG. 1*b*.

FIG. 2 details a modified design of a wick or emitter assembly in comparison to the wicks shown in FIG. 1. Wick assembly 16 is comprised of a center electrode assembly which is made of ceramic fibers 8 in which are embedded stainless steel wires 9. Fibers 8 are preferably formed into a plurality of elongated capillament bundles 8*a* as shown. The fibers 8 may be braided or twisted, with wires 9 either extending straight therein or intertwined with the fibers. This core is covered by a glass fiber braid in the form of a sleeve 10 preferably comprised of a plurality of separate capillament bundles of fine fibers or filaments which are exposed at 10*b* at the top of the assembly. An outer cover of glass 11 may also be provided if the sleeve 10 does not provide a sufficiently strong, liquid impervious outer layer. In this design the inner conductive fiber core contacts the electrode 5, which preferably extends at least partially into the inner core of capillaments 8*a* as shown. It also holds the liquid that is transferred to the glass fiber braid. The core wires 9 help shape the electric field which in turn effects the vapor aerosol pattern and also the air ion output. The outer glass fiber braid 10 moves the liquid by capillary action from bottom fibers 10*a* to the top through exposed top fibers 10*b* where the electrostatic field breaks down the surface tension of the liquid, and from the very" rinds 10*c* of the glass fibers the liquid is converted to vapor and/or aerosols and released. Capillament bundles 8*a* also assist in moving the liquid through the assembly 16 by wicking or capillary action.

This design also is a very effective air ion emitter. This illustration is an example of the concept of using a number of materials which together have the desired properties of porosity, conductance, and capillary action, and will generate vapor and/or aerosols when electrified by a voltage high enough to break the surface tension of the desired liquid.

Figure 3:
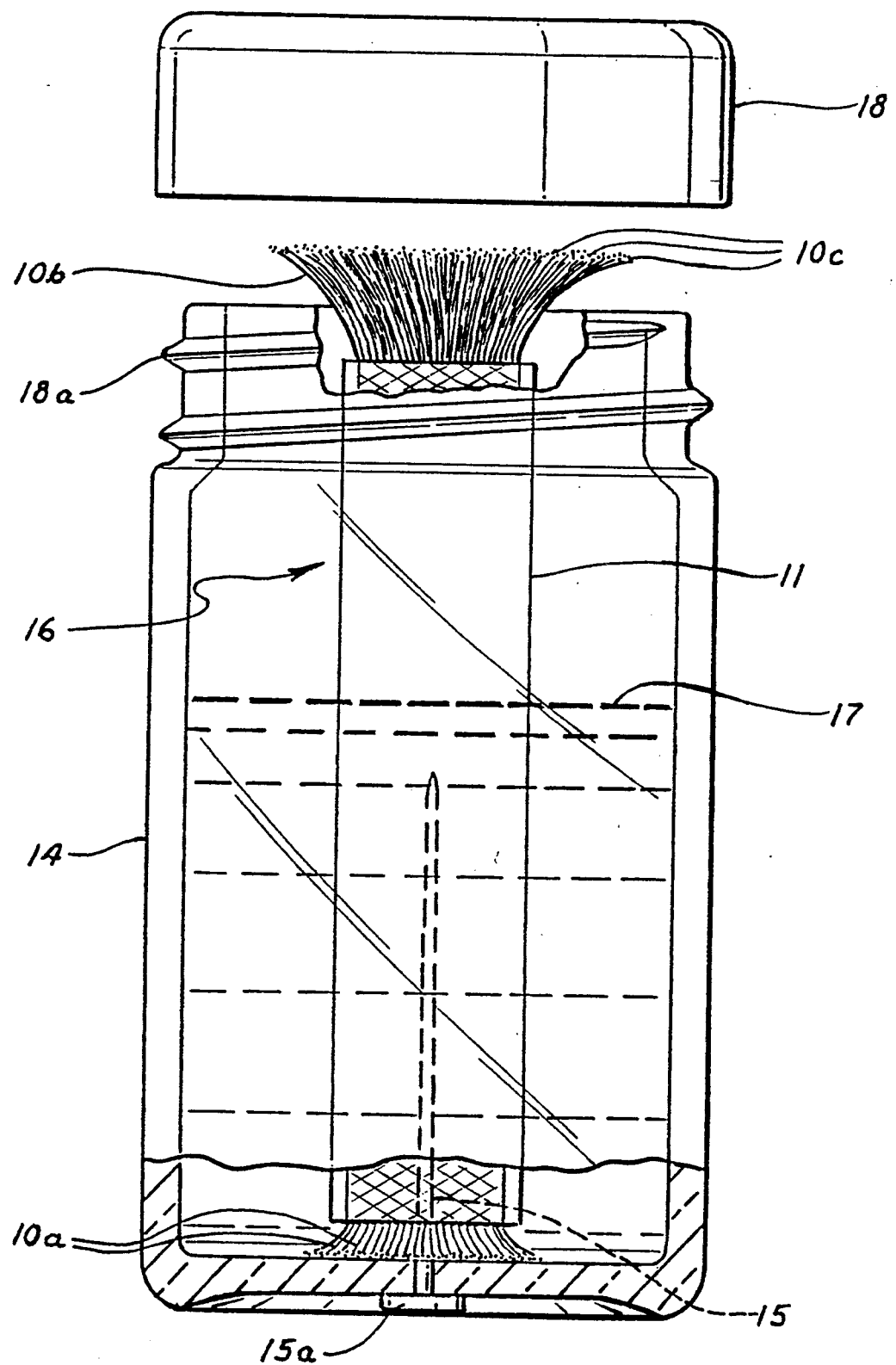
FIG. 3 shows the installation of the "wick" assembly shown in FIG. 2 within a glass bottle. This embodiment is a self-contained liquid storage and vapor/aerosol dispensing device.
Figure 4:
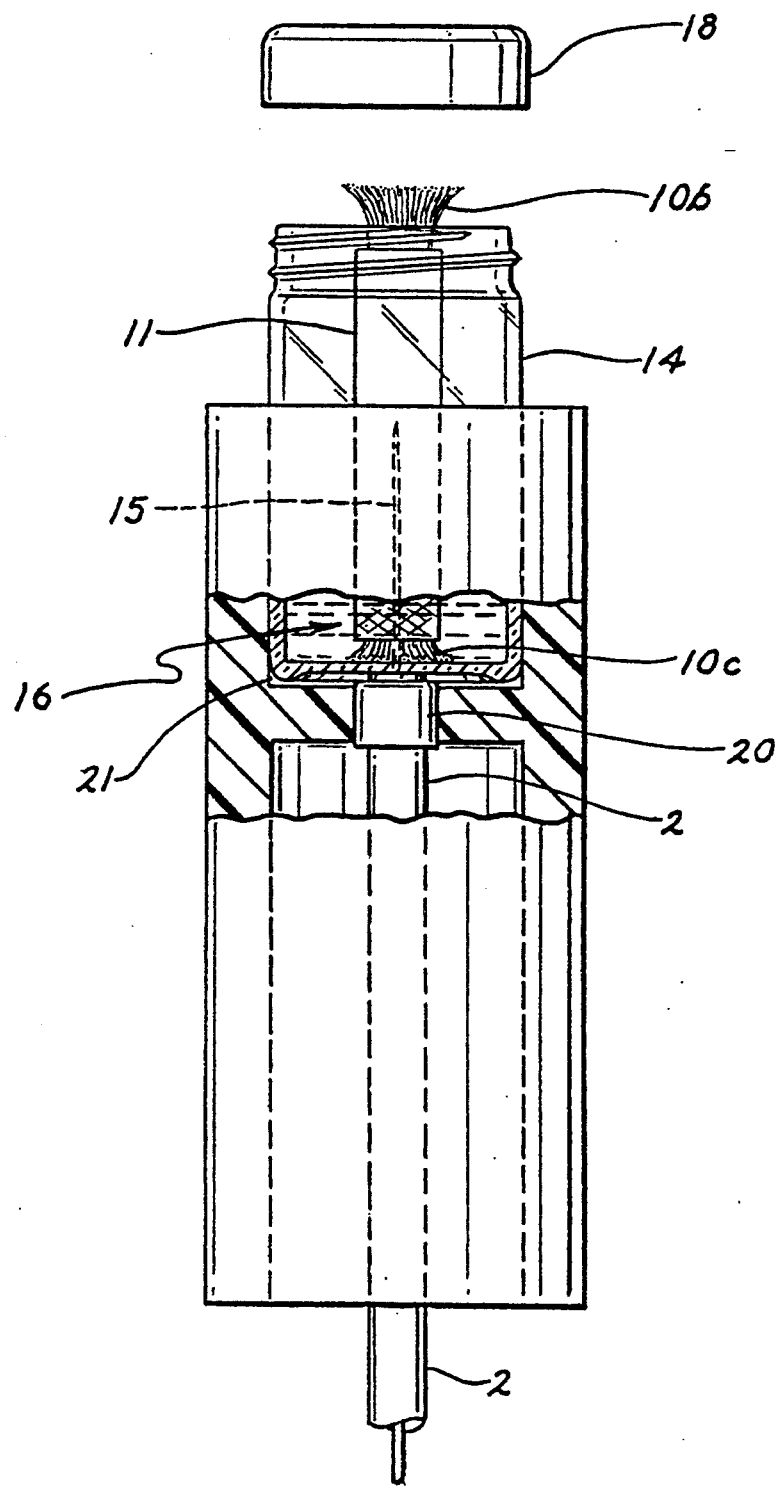
FIG. 4 is an illustration of an embodiment of a means to hold the device of FIG. 3 and apply an electrostatic charge to it.
Figure 6:
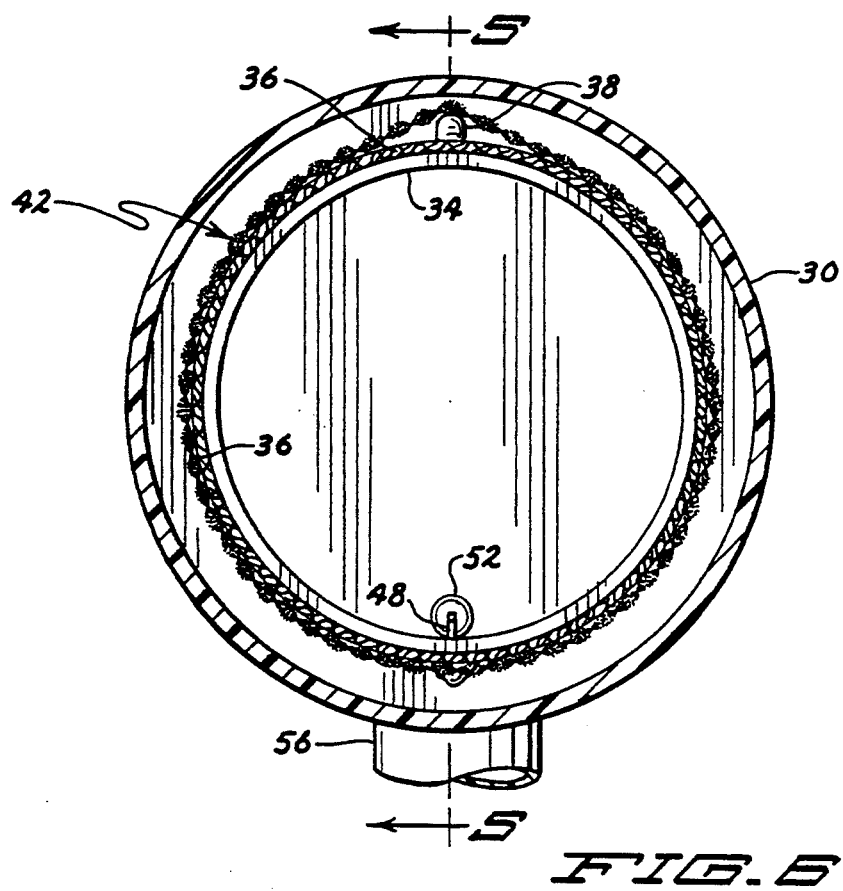
FIG. 6 is an end view of the assembly of FIG. 3, partially in section, taken along lines 6—6 of FIG. 5 and FIG. 9.

FIG. 3 is a preferred embodiment of a device that will also provide a means of containing the liquid that would be supplied to the wick assembly 16 of FIG. 2. In this embodiment a glass bottle 14 contains the wick assembly 16 and has a high voltage electrode 15 which extends through the bottom of the bottle. It also has a contact terminal 15*a* on the bottom of the bottle in order to provide a means of supplying a charge to the wick assembly 16. The desired liquid 17 is contained within the bottle and is continuously moved to the top of the wick by capillary action. That action is enhanced by the extension of fiber end segments 10*a* into the liquid at the lower end of wick assembly 16. The bottle can be sealed by a cap 18 and stored for later use without loss of liquid due to evaporation or spilling. This embodiment is a self-contained system that will generate vapor and/or aerosols and also air ions when it is provided a high voltage DC signal to the base electrode and the bottle cap 18 is removed. A threaded cap 18 may be used for attachment to threads 18*a* on bottle 14.

FIG. 4 shows an embodiment of a device that holds the vaporizing bottles detailed in FIG. 3. The device is comprised of an insulating support 19 made of porcelain, glass, plastic, or similar material. A high voltage DC signal is supplied to the contact terminal connector 20 by a high voltage wire 2. The electrode contact 15*a* of the bottle 14 makes contact with the power contact 20 as shown. This provides power to the wick assembly 16 and causes the vapor and/or aerosols to emanate from the top of the bottle into the air. The bottle 14 is secured within the recess 21 of the support column.

FIG. 5 is an illustration of an embodiment of a "vaporizing emitter." The emitter is comprised of an outer housing 30 made of nonconductive, plastic material, such as polyvinylchlcride. Housing 30 has a sealed end 30*a*, of an aerodynamic shape as shown to enhance air flow thereover. The opposite end 30*b* of housing 30 is open to serve as a discharge end for the emitter assembly. Housing 30 serves as a device for enclosing and supporting a vaporizing emitter assembly. The base or inlet end of that assembly is formed by a plastic base plate or disc 32 which extends transversely across housing 30 as shown in FIG. 5. A tubular support 34, also made of nonconductive, plastic material, such as polyvinylchloride, or, preferably high density polyethylene, is secured at one end to base plate 32. As shown, this may be accomplished by extending the rear end of tubular support 34 into slots formed in base plate 32 for a friction fit and/or adhesive attachment thereto. The opposite, forward end of tubular support 34 is recessed rearwardly from the open, discharge end 30*b* of housing 30, as shown. Preferably, a gauzelike wick sleeve or annular member 36 is placed around the outside of tubular support 34 at its forward end as shown. As hereinafter set forth, wick 36 serves to retain liquid and prevent its drippage downwardly within housing 30, and also serves as a pathway for the flow of liquid to an outermost, vaporizing emitter sleeve or annular element 42.

A selected liquid to be vaporized and utilized as a conditioning fluid for the atmosphere within a building is introduced under pressurized control from a pump (not shown) into a liquid supply tube 38 which extends into housing 30 as shown in FIG. 5. With housing 30 oriented horizontally as shown in FIG. 5, the inner end of liquid tube 38 preferably extends horizontally along the top side thereof, at a 12 o'clock position as viewed in FIG. 6. Tube 38 is provided with an elongated slit 40 at its outer end, just rearwardly from its closed terminal end. Elongated slit 40 permits liquid to be distributed over a substantial portion of the length or height of wick sleeve 36. With the assembly oriented horizontally as shown in FIGS. 5 and 6, the liquid will flow around the opposite sides of sleeve 36 and saturate it. This sleeve holds the liquid and prevents it from dripping downwardly onto the bottom side of housing 30. Sleeve 36 may be made of cotton, other fabric, or suitable gauzelike material which is capable of being saturated with and holding a liquid.

Embracing wick sleeve 36 is an outermost, annular element or sleeve-shaped vaporizing emitter 42. Emitter sleeve 42 is slipped over the outside of the slit end of liquid supply tube 38, as well as around the outside of wick sleeve 36, at the location shown in FIGS. 5 and 6.

Emitter sleeve 42 is preferably comprised of fibers woven in a ribbonlike configuration to form bundles of distinct capillaments extending longitudinally within sleeve 42 in a direction generally parallel to the longitudinal direction of extent of tubular support 34 and housing 30, as shown most clearly in FIG. 7. Those capillament bundles are comprised of individual lengths of fibers 44, such as polyester, which terminate at their outer ends in a plurality of distinct fiber bundles 46. As shown in FIGS. 5 and 7, each of the bundles 46 is of a brushlike configuration comprised of a plurality of fibers having terminal tips 46a which serve as vapor release sites. With reference to FIG. 5, it may be seen that bundles 46 extend slightly (e.g., one-eighth inch) beyond the open end of tubular support 34, but are recessed rearwardly inside of the open, discharge end 30b of housing 30. This arrangement insures the proper, free discharge of charged, conditioning vapors from bundles 46 in a somewhat constrained spray pattern as illustrated at 70 in FIG. 9.

High voltage, direct current (DC) power is introduced to the emitter assembly through a conductor lead or wire 50 contained within insulation 52 as shown in FIGS. 5 and 6. At its terminal end, lead wire 50 is configured into a hook configuration 48 as shown in FIGS. 5 and 6 to extend through and be secured within a pair of closely spaced apertures 54 and 55 extending through the wall of tubular support 34 under wick sleeve 36 and emitter sleeve 42. Terminal contact 48 is thus in direct physical contact with wick sleeve 36. If wick sleeve 36 is not utilized, then conductor terminal 48 would be in direct contact with the inner face of emitter sleeve 42.

Both liquid supply tube 38 and power supply lead 50, 52 are advantageously contained within a supply conduit 56 as shown in FIGS. 5 and 6. That conduit is also preferably made from the same plastic material from which housing 30 is formed, and may be secured thereto through an aperture in the wall of housing 30 by friction fit and/or the use of adhesives. As hereinafter set forth with respect to FIG. 9, supply conduit 56 also serves as a support for housing 30 to hold and support the entire emitter apparatus within an air duct.

FIGS. 7 and 8 illustrate in detail on an enlarged scale a fragmentary portion of the ribbonlike vaporizer emitter 42. The plurality of longitudinally extending capillament bundles 62 comprised of individual fibers 44 are held and separated into the plurality of bundles 62 as shown by the use of cross woven threads 58. Nonconductive fibers 58 are interwoven around the separate capillament bundles 62 in the manner shown in FIGS. 7 and 8 to separate the bundles of fibers 44 into the distinct capillament bundles 62 as shown. In order to enhance the conduction of the electrical current from lead wire 50 through the emitter ribbon 42, a plurality of metallic fibers or wires 60 may be utilized. As is also shown in FIGS. 7 and 8, those conductive metal fibers, strips, or wires 60 are interwoven across or transversely of the capillament bundles 62 in the same manner as nonconductive fibers 58, but on opposite sides thereof and intermittently along the length of the capillament bundles 62 so as to form a complete emitter ribbon 42. The conductive fibers or strands 60 are not required, but are believed to assist in the conduction of the electrical charge to and through the emitter ribbon 42.

In operation, the desired liquid for atmosphere conditioning purposes, such as an aromatic liquid, insecticide, disinfectant or fungicide, is introduced into liquid supply tube 38 at a controlled rate. This is accomplished by a supply pump connected to a liquid storage reservoir, both of which are not shown. The precisely metered fluid is released onto the wick sleeve 36 through slot 40 in tube 38. As the wick 36 becomes saturated with the liquid, it is transferred by direct physical contact with the woven vaporizing sleeve 42, with the fluid flowing primarily along the capillament bundles 62 towards the brushlike terminal bundles 46. The high voltage direct current (negative) is supplied to the wick assembly by way of electrical contact 48 on the end of conductor wire 50 and provides a source of electrons which are driven at a very high electrostatic force towards a ground beyond the open, discharge end 30b of housing 30. That ground may comprise the duct work itself, or other electrical ground in the building into which the vapor is being discharged. The electrons are driven off the terminal ends 46a of the bundles 46, with the liquid also being discharged from the bundle tips 46a in the form of an electrostatically charged vapor and/or microaerosols. The DC negative voltage utilized is so high, 5000 to 50,000 volts, that the negative electrons released from the conductor lead 52 migrate to the nearest available conductor medium, by capacitive coupling mode. Thus, the electrons move to the capillaments 62, and through their individual fibers 44, and thus into the conditioning fluid contained in the ribbonlike emitter 42. This movement of electrons would happen even without the metallic conductor strips or fibers 60 interwoven within the emitter element 42. However, as noted above, those conductive strips or fibers do enhance electron flow through the emitter. A cloud or stream of negatively charged vapor and aerosol molecules is released from the fiber tips 46a into the air or air stream, with these molecules kinetically interacting with the air molecules and airborne particles, such as dust. The airborne particles receive the free, negative electrons and ultimately seek and find an earth ground (positive), by way, for example, of the building duct work.

Figure 9:
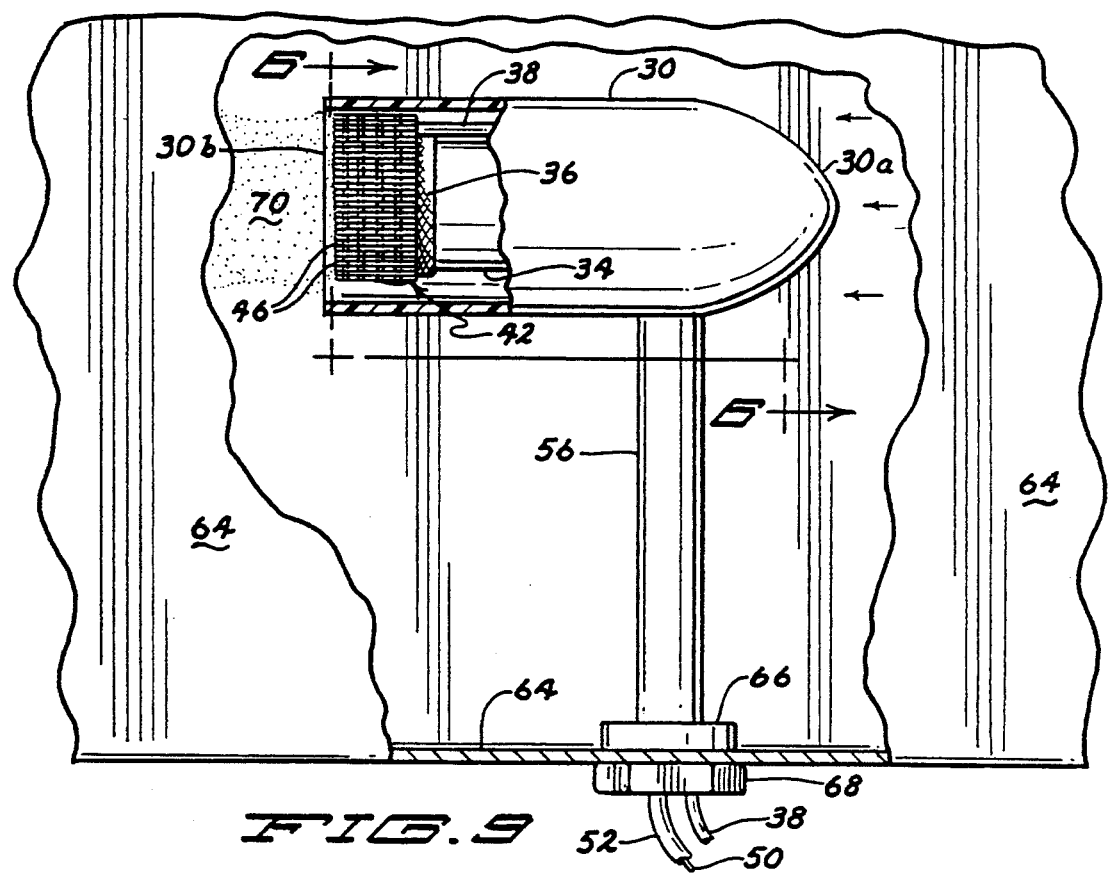
FIG. 9 is a side elevation view, partially broken away, of the electrostatic vaporization assembly of FIG. 5 mounted within an air handling duct of a building.

With respect to the duct application, FIG. 9 discloses the emitter assembly described above mounted within a building duct 64. Such a duct would be one which handles air being circulated through a building for air conditioning or ventilation purposes. Supply conduit 56 is inserted through an opening in the duct wall, and secured to the duct by means of friction fit of a collar 66 within the aperture, in combination with an outer, locking flange nut 68. With such a mounting, supply conduit 56, which is rigid plastic, serves to hold and support housing 30 within the air stream of duct 64 as illustrated in FIG. 9. In the embodiment shown, the support 56 in the form of a supply conduit is preferably inserted through the bottom of the duct so as to be disposed in a upright position. The aerodynamic configuration given to the end 30a of housing 30 enhances air flow over the housing and minimizes resistance to air flow through the duct 64. The above-referenced cloud of vapor is illustrated at 70 in FIG. 9 at the outlet end 30b of housing 30. Thus, as the vapor and charged molecules exit housing 30, they become entrained in the air stream moving over housing 30 from right to left as viewed in FIG. 9. The high voltage DC current is supplied through conductor wire or lead 50 and the conditioning liquid is supplied through tube 38, both of which extend through supply conduit 56 into the interior of emitter housing 30, as described above. The air thus conditioned by the vapors discharging from emitter housing 30 is carried by the air circulating through duct 64 through the various rooms of a building.

FIG. 10 illustrates a further embodiment of the emitter apparatus of this invention, which could also be utilized to either discharge conditioned vapor directly into a room space, or to indirectly condition the atmosphere of a building by discharge into the air stream of an air handling duct as described above with respect to FIG. 9. This embodiment utilizes the same basic housing 30, with a supply conduit 56 through which electrical lead wire 50 and liquid supply tube 38 are directed. A plastic base plate 32 is again utilized, and extends transversely of the housing 30. The base plate is referenced in FIG. 10 as element 32a. In order to enhance the power and intensity of charged vapor discharge, a plurality of concentric, vaporizing emitters 42a, 42b and 42c are utilized. For that purpose, a plurality of concentric tubular supports 34a, 34b, and 34c are utilized in the manner shown, each being secured at its base end without base plate 32a. Those separate tubular members serve to separately support wick sleeves 36 inserted thereover. The separate, emitter sleeves 42a, 42b, and 42c are then slipped over the wick sleeves 36 in embracing relation to each of the tubular supports 34a, 34b, and 34c as described above with respect to FIG. 5.

Separate liquid supply tubes 38a, 38b, and 38c extend from main liquid supply tube 38 by way of T-fittings 72 and elbow fitting 74. The outer, terminal ends of those liquid supply tubular segments 38a, b, and c are closed in the same manner as described above with respect to FIG. 5, and each of the liquid supply tubular segments has an elongated slit 40 near its outer end through which liquid is discharged along the length of wicks 36. However, only a single electric supply conductor 50 may be utilized in the manner shown in FIG. 10, with its terminal contact 48 being secured through apertures in the wall of tubular support 34a in the same manner as described with respect to FIG. 5 and its apertures 54 and 55. Thus, the electrical charge is first supplied to outermost emitter 42a. The high voltage direct current is of sufficient magnitude that the electrical charge moves inwardly to successively inwardly disposed emitter sleeves 42b and 42c through the mode of capacitive coupling. Thus, all three emitter sleeves 42a, 42b, and 42c are charged with high voltage, negative current. The liquid contained in the emitter sleeves is charged and the liquid vaporizes in the same manner as described above with respect to FIGS. 5-9.

It is to be noted that the terminal ends of the successive, concentric emitter sleeves are at staggered locations with respect to discharge end 30b of housing 30. For that reason, tubular supports 34a, b, and c are made of successively greater lengths, with support 34b terminating laterally outwardly beyond innermost support 34a and support 34c extending to the greatest extent outwardly, beyond the terminal end of support tube 34b. This progressive staggering of the tubular supports more outwardly from the outermost to the innermost one of the concentric tubular supports has been found to enhance the movement of charged electrons from outermost emitter sleeve 42a inwardly to the next inwardly disposed emitter sleeve 42b, and finally to innermost emitter sleeve 44c. Reference numeral 70 again illustrates the cloud or stream of charged vapor discharging from the entire emitter assembly.

It is to be noted that either the emitter assembly of FIG. 10, or that illustrated in FIG. 5 may be utilized to directly condition a room space, without being mounted inside of an air handling duct. For that purpose, the supply conduit 56 would be configured and sized to serve as a handle for holding the emitter assembly for manual conditioning of a room space.

It is also anticipated that the emitter or wick assembly shown in FIG. 2 could be utilized in a duct application to disperse charged, conditioning vapors into the air stream of a building. This would be done in the same manner described above with respect to the housing 30 and emitter assembly contained therein as illustrated in a duct mounting arrangement in FIG. 9. In such an application, the liquid supply tube 38 would be directed to the outside of emitter sleeve 10 along its length, and the electrical conductor wire 50 would be introduced through the duct into contact with the wick assembly in the manner illustrated with respect to electrode 5 in FIG. 2.

In summary, the embodiments of the devices disclosed herein serve to illustrate a novel method and apparatus for generating liquid based aerosols, vapors, and also air ions with a variety of means of control over the quantity of vapor and/or aerosols generated. The fundamental basis for all of these methods and disclosed devices is the use of electrostatic charges applied to a semiconductive, wick-light, porous, capillament assembly which is also supplied with the desired liquid which is to be vaporized.

The electrostatically charged vapor or aerosol may be injected into the air handling system of a building as described above to odorize by the use of essential oils or perfumes or to disinfect by the use of fungicides, bactericides, fumigants, insecticides, disinfectants, and the like. In this manner, micro-organisms such as bacteria, fungus, mold, and the like which collect in air handling and air conditioning systems, and particularly on the surfaces of ducts and air handling equipment, may be treated by such electrostatically charged vapors so as to be neutralized and controlled.

The foregoing description of the preferred embodiments of this invention has been presented for the purposes of illustration and description. It is not intended to be exhaustive or to limit the invention to the precise forms disclosed. Many modifications and variations are possible in the light of the above teachings. It is intended that the scope of the invention be limited not by this detailed description, but rather by the claims appended hereto.

What is claimed is:

1. Vaporizing emitter apparatus for generating electrostatically charged aerosols and vapors comprising:
   a capillary unit of elongated, tubular configuration having a vapor dispensing end, said capillary unit comprising an elongated tubular support and a vaporizing emitter sleeve disposed and supported on the tubular support in embracing relation thereto, said emitter sleeve being comprised of nonconductive fibers woven in an annular configuration to comprise a plurality of capillament bundles, with each bundle comprising a plurality of elongated fibers extending longitudinally of said elongated tubular support and terminating at their free ends in a bundle of freely extending fiber tips at the vapor dispensing end of said capillary unit from which vapor is emitted;

an electrical conductor having a contact terminal defining a single electrode unit for conducting high voltage direct current to said emitter sleeve disposed in close proximity to said emitter sleeve;

means for the controlled supply of liquid to said capillary unit, whereby liquid passes through said capillary unit in proximity to said electrode and is electrostatically charged and dispensed as vapor or aerosol from said fiber tips at the dispensing end of said capillary unit.

2. Apparatus as defined in claim 1 wherein:
said capillary unit further comprises a wick sleeve capable of holding and transferring liquid and supported around said tubular support between the tubular support and the emitter sleeve.

3. Apparatus as defined in claim 2 wherein:
said wick sleeve is comprised of polyester fibers.

4. Apparatus as defined in claim 2 wherein:
said contact terminal of said electrical conductor is in direct, physical contact with said wick sleeve.

5. Apparatus as defined in claim 1 wherein:
said contact terminal is looped through apertures in the wall of said tubular support and supported thereon.

6. Apparatus as defined in claim 1 wherein:
said tubular support is nonconductive.

7. Apparatus as defined in claim 1 wherein:
said freely extending fiber tips of each of said plurality of capillament bundles extend outwardly beyond one end of said elongated tubular support at said vapor dispensing end of said emitter.

8. Apparatus as defined in claim 1, and further including:
a source of high voltage direct current connected to said electrical conductor.

9. Apparatus as defined in claim 1 wherein:
said means for the controlled supply of liquid to said capillary unit comprises a liquid supply tube, said supply tube having a horizontally extending segment which extends along the top side of said capillary unit with the capillary unit disposed horizontally for vapor dispensing, and said liquid supply tube having a discharge aperture through which conditioning liquid is released onto the top of said capillary unit.

10. Apparatus as defined in claim 1 and further comprising:
a supporting housing containing and supporting said capillary unit, said housing having an open dispensing end terminating at a location adjacent to the dispensing end of the capillary unit; and
means for supporting the housing comprising a supply conduit affixed to the housing for supporting the housing and the entire emitter apparatus within a duct or other air flow passage of a central air conditioning system, said electrical conductor extending through said supply conduit and into the housing; and a liquid supply tube for said liquid extending within and through said supply conduit and into said housing, said liquid supply tube having a discharge end positioned adjacent to the emitter sleeve.

11. Apparatus as defined in claim 1, and further comprising:
a supporting housing containing and supporting said capillary unit, said housing having an open dispensing end terminating at a location adjacent to the dispensing end of the capillary unit, said fiber tips terminating at their end extremities inside of the open, dispensing end of said housing, and outside of and beyond the adjacent end of the tubular support.

12. Apparatus as defined in claim 1, and further comprising:
a supporting housing containing and supporting said capillary unit for mounting within an air conditioning duct of a building, said housing being closed at one end and having an opposite, open dispensing end terminating at a location adjacent to the dispensing end of the capillary unit, said open dispensing end being downstream of the closed end with respect to the direction of air flow over the housing in an air conditioning duct.

13. Apparatus as defined in claim 12 wherein:
said closed end of said housing tapers in a direction away from the open, dispensing end of said housing so as to present a streamlined, aerodynamic configuration to air flowing over said housing.

14. Vaporizing emitter apparatus for generating electrostatically charged aerosols and vapors comprising:
a capillary unit of elongated, tubular configuration having a vapor dispensing end, said capillary unit comprising an elongated tubular support and a vaporizing emitter sleeve disposed and supported on the tubular support in embracing relation thereto, said emitter sleeve being comprised of nonconductive fibers woven in an annular configuration as a ribbon to comprise a plurality of capillament bundles, with each bundle comprising a plurality of elongated fibers extending longitudinally of said elongated tubular support and terminating at their free ends in a bundle of freely extending fiber tips at the vapor dispensing end of said capillary unit from which vapor is emitted, said elongated fibers being woven in said ribbon and held in the capillament bundles by threads or fibers cross-woven through said ribbon and extending transversely to the longitudinal direction of extent of the elongated fibers;

an electrical conductor having a contact terminal defining an electrode for conducting high voltage direct current to said emitter sleeve disposed in close proximity to the emitter sleeve; and means for the controlled supply of liquid to the capillary unit, whereby liquid passes through the capillary unit in proximity to the electrode and is electrostatically charged and dispensed as vapor or aerosol from the fiber tips at the dispensing end of the capillary unit.

15. Apparatus as defined in claim 14 wherein:
said emitter sleeve further comprises a plurality of metallic fibers or strips cross woven therethrough and extending transversely to the longitudinal direction of extent of said bundles, said metallic strips or fibers being electrically conductive to assist in conducting the aforesaid high voltage direct current to and through the emitter sleeve.

16. Vaporizing emitter apparatus for generating electrostatically charged aerosols and vapors comprising:

a plurality of capillary units of tubular configuration positioned concentrically, one inside of the other, each of said capillary units having a dispensing end from which vapor is emitted, and comprising an elongated tubular support and a vaporizing emitter sleeve disposed and supported on the tubular support in embracing relation thereto, each of said emitter sleeves being comprised of nonconductive fibers woven in an annular configuration to comprise a plurality of capillament bundles, with each bundle comprising a plurality of elongated fibers extending longitudinally of said elongated tubular supports and terminating at their free ends in a bundle of freely extending fiber tips at the vapor dispensing end of each of said capillary units, from which vapor is emitted, with said tubular supports being concentrically disposed with respect to each other and of gradually increasing diameter, and with the vapor dispensing ends of the capillary units being disposed at the same end of the emitter apparatus adjacent to each other;

an electrical conductor having a contact terminal defining an electrode for conducting high voltage direct current to the emitter apparatus and disposed in close proximity to the emitter sleeve of at least one of the plurality of capillary units; and means for supplying liquid to said capillary units, whereby liquid on the emitter sleeves of the adjacent capillary units is electrostatically charged with vapor being dispensed from the freely extending fiber tips at the vapor dispensing end of each of the capillary units.

17. Apparatus as defined in claim 16 wherein:

said electrode is disposed in close proximity to the emitter sleeve of only one of the plurality of capillary units, whereby liquid on the emitter sleeve of said one capillary unit is directly electrostatically charged and the liquid on the emitter sleeves of the adjacent capillary units is electrostatically charged by capacitive coupling between the adjacent capillary units.

18. Apparatus as defined in claim 17 wherein:

said electrode is disposed in close proximity to only the emitter sleeve of the radially outermost one of the plurality of capillary units.

19. Apparatus as defined in claim 16 wherein:

the emitter apparatus has a base end opposite the vapor-dispensing ends of the plurality of capillary units; and the vapor-emitting, freely-extending fiber tips of each of the capillary units being disposed at progressively staggered distances from said base end, with the radially innermost capillary unit having its freely extending fiber tips farthest away from the base end of the emitter apparatus.

* * * * *

UNITED STATES PATENT AND TRADEMARK OFFICE
CERTIFICATE OF CORRECTION

PATENT NO. : 5,382,410
DATED : January 17, 1995
INVENTOR(S) : Mark E. Peltier

It is certified that error appears in the above-indentified patent and that said Letters Patent is hereby corrected as shown below:

In the BREIF SUMMARY OF THE INVENTION: Col. 3, line 25, after "braiding," delete "class" and substititue --glass--therefor.

Signed and Sealed this

Twelfth Day of September, 1995

Attest:

BRUCE LEHMAN

*Attesting Officer*          *Commissioner of Patents and Trademarks*